United States Patent [19]

Brack

[11] B 3,992,405
[45] Nov. 16, 1976

[54] CATIONIC DYESTUFFS

[75] Inventor: Alfred Brack, Leverkusen, Germany

[73] Assignee: Bayer Aktiengesellschaft, Leverkusen, Germany

[22] Filed: July 28, 1972

[21] Appl. No.: 276,026

[44] Published under the second Trial Voluntary Protest Program on February 3, 1976 as document No. B 276,026.

[30] Foreign Application Priority Data

July 29, 1971 Germany............................ 2138029

[52] U.S. Cl. ...................... 260/326.5 B; 260/326.9; 8/1 D; 8/85 R
[51] Int. Cl.² ........................................ C07D 209/60
[58] Field of Search ................... 260/326.9, 326.5 B

[56] References Cited
UNITED STATES PATENTS 3,347,865  10/1967  Brack et al. ...................... 260/313.1

FOREIGN PATENTS OR APPLICATIONS 1,074,786  7/1967  United Kingdom.............. 260/326.9

Primary Examiner—Joseph A. Narcavage
Attorney, Agent, or Firm—Plumley & Tyner

[57] ABSTRACT

Cationic dyestuffs of the formula

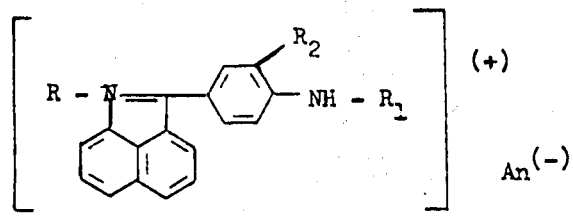

wherein R represents an alkyl, cycloalkyl, aralkyl or aryl radical or an alkylene radical bonded to the naphthalene ring in the β-position, $R_1$ represents an alkyl, cycloalkyl or aralkyl radical, $R_2$ represents hydrogen or an alkyl, aralkyl, alkoxy, aralkoxy, hydroxyl, amino or acylamino radical and $An^{(-)}$ represents an anion, are suitable for dyeing and printing synthetic and natural materials, especially of polyacrylic fibers.

10 Claims, No Drawings

CATIONIC DYESTUFFS

The subject of the present invention are new cationic dyestuffs of the general formula

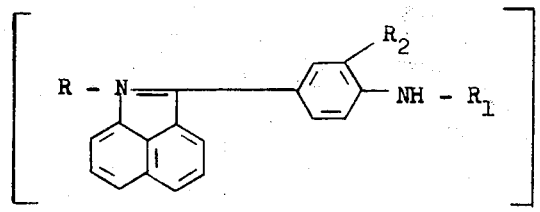

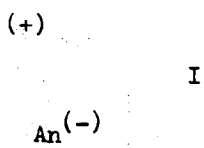

wherein
- R represents an alkyl, cycloalkyl, aralkyl or aryl radical or an alkylene radical bonded to the naphthalene ring in the β-position,
- $R_1$ represents an alkyl, cycloalkyl or aralkyl radical and is a branched alkyl radical, an alkyl radical substituted by non-ionic radicals, or a cyclohexyl, benzyl or phenylethyl radical if $R_2$ represents hydrogen,
- $R_2$ represents hydrogen or an alkyl, aralkyl, alkoxy, aralkoxy, hydroxyl, amino or acylamino radical and An $^{(-)}$ represents an anion, and wherein the cyclic and the acyclic radicals may contain non-ionic substituents, and wherein other (possibly non-ionically substituted) carbocyclic or heterocyclic rings may be fused to the rings, as well as processes for the manufacture of these dyestuffs, their use for dyeing, printing and bulk dyeing of natural and synthetic materials, and the materials dyed and printed with these dyestuffs.

Preferred dyestuffs correspond to the general formula

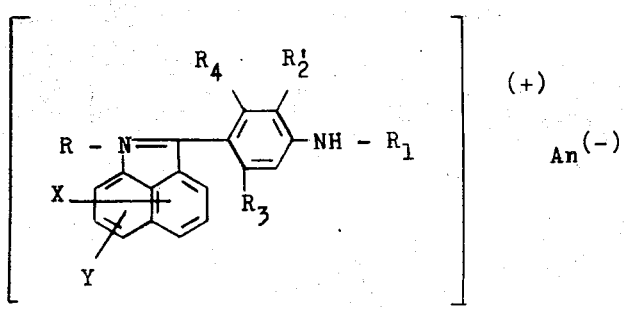

wherein
R represents an alkyl, cycloalkyl, aralkyl or aryl radical or an alkylene radical bonded to the naphthalene ring in the β-position,
- $R_1$ represents an alkyl, cycloalkyl or aralkyl radical,
- $R_2'$ represents an alkyl, aralkyl, alkoxy, aralkoxy, hydroxyl, amino or acylamino radical,

I

- $R_3$ represents hydrogen, halogen or an alkyl, alkoxy, hydroxyl, amino or acylamino radical,
- $R_4$ represents hydrogen, halogen or an alkyl, alkoxy, hydroxyl, amino or acylamino radical,
- X represents hydrogen, halogen or a hydroxyl, alkoxy, alkyl, amino, acylamino, amidosulphonyl, nitrile, amidocarbonyl or alkoxycarbonyl group,
- Y represents hydrogen, halogen or a hydroxyl, alkoxy, alkyl, amino, acylamino, amidosulphonyl, nitrile, amidocarbonyl or alkoxycarbonyl group,
- An $^{(-)}$ represents an anion and the radicals R, $R_1$, $R'_2$, $R_3$ and $R_4$ can contain nonionic substituents.

Particularly preferred dyestuffs are those of the formula

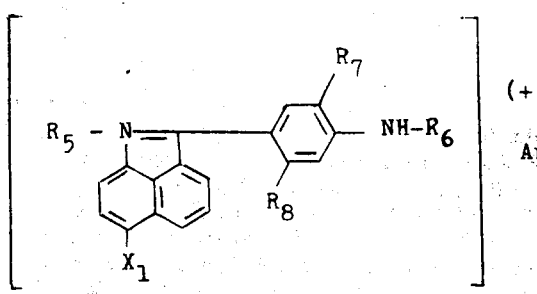

III wherein
- $R_5$ represents an alkyl radical with at most 6 C atoms,
- $R_6$ represents an alkyl radical with at most 6 C atoms or a benzyl radical,
- $R_7$ represents an alkyl or alkoxy radical with at most 4 C atoms,
- $R_8$ represents hydrogen or an alkyl or alkoxy radical with at most 4 C atoms,

II $X_1$ represents hydrogen, chlorine or bromine and $An^{(-)}$ represents an anion and the radicals $R_5$, $R_6$, $R_7$ and $R_8$ can contain non-ionic substituents.

$R_{14}$ represents an ethyl, β-cyanoethyl or β-chloroethyl group, $X_1$ represents hydrogen, chlorine or bromine and $An^{(-)}$ represents an anion and

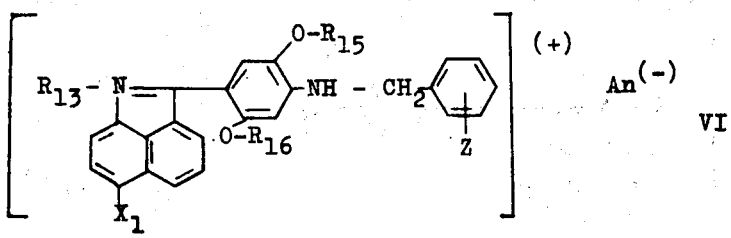

Dyestuffs of the formula III in which $R_7$ and $R_8$ independent of one another represent an alkoxy radical with at most 4 C atoms are particularly singled out.

Of these preferred dyestuffs, those of the formula

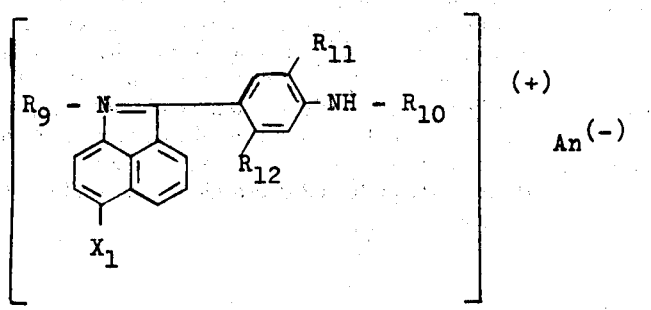

wherein $R_{13}$ represents a methyl or ethyl group,
$R_{15}$ represents a methyl or ethyl group,
$R_{16}$ represents a methyl or ethyl group,
$X_1$ represents hydrogen, chlorine or bromine,
Z represents hydrogen, chlorine or a methyl, methoxy or ethoxy group and
$An^{(-)}$ represents an anion.

Amongst the dyestuffs of the formulae I to IV, those should in turn be especially singled out in which the radical $R_1$ or $R_6$ or $R_{10}$ represents a β-cyanoethyl, β-chloroethyl or benzyl group.

Non-ionic substituents in the sense of the present invention are the non-dissociating substituents which are customary in dyestuff chemistry, such as fluorine, chlorine and bromine; alkyl groups, especially straight-chain or branched alkyl radicals with 1 – 6 C atoms; aralkyl radicals; alkenyl radicals; aryl radicals; alkoxy radicals, especially alkoxy radicals with 1 – 4 C atoms; aralkoxy radicals; aryloxy radicals, alkylthio radicals, preferably alkylthio radicals with 1 – 3 C atoms; aralkylthio radicals; arylthio radicals; nitro; nitrile; alkoxycarbonyl, preferably those with an alkoxy radical with 1 – 4 C atoms; the formyl radical; alkylcarbonyl radicals, especially those with an alkyl group with 1 – 4 C atoms; arylcarbonyl; aralkylcarbonyl radicals; alkoxycarbonyloxy radicals, preferably with an alkyl group with 1 wherein
$R_9$ represents a methyl, ethyl, n-propyl, n-butyl, β-cyanoethyl or β-chloroethyl group,
$R_{10}$ represents a methyl, ethyl, n- and iso-propyl, n- and iso-butyl, n- and iso-amyl, β-cyanoethyl, γ-cyanopropyl, β-chloroethyl, β-hydroxycarbonylethyl, β-amidocarbonylethyl, benzyl, 4-methylbenzyl, 4-chlorobenzyl or 4-lower-alkoxybenzyl group,
$R_{11}$ represents a methyl, ethyl, methoxy or ethoxy group,
$R_{12}$ represents hydrogen or a methyl, ethyl, methoxy or ethoxy group,
$X_1$ represents hydrogen, chlorine or bromine and $An^{(-)}$ represents an anion,
are the most valuable.

Further dyestuffs to be singled out as being particularly valuable are those of the formulae

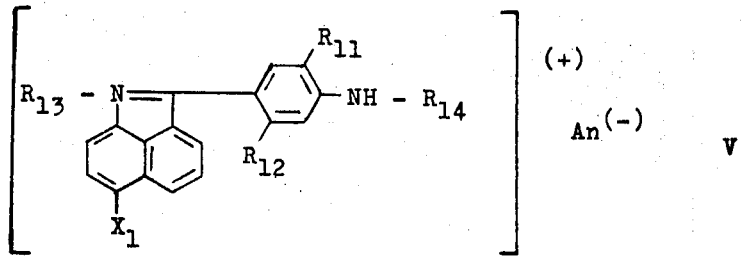

wherein
$R_{11}$ represents a methyl, ethyl, methoxy or ethoxy group,
$R_{12}$ represents hydrogen or a methyl, ethyl, methoxy or ethoxy group,
$R_{13}$ represents a methyl or ethyl group, – 4 C atoms; alkylcarbonylamino radicals, preferably with an alkyl group with 1 – C atoms, arylcarbonylamino radicals; alkylsulphonylamino radicals, preferably with an alkyl group with 1 – 3 C atoms; arylsulphonylamino groups, ureido, N-aryl-ureido or N-alkylureido, aryloxycarbonylamino and alkyloxycarbonylamino; carbamoyl; N-alkyl-carbamoyl; N,N-dialkyl-carbamoyl; N-alkyl-N-aryl-carbamoyl; sulphamoyl; N-alkyl-sulphamoyl; N,N-dialkyl-sulphamoyl, with 1 – 4 C atoms preferably being present in the alkyl radicals mentioned; carboxylic acid alkyl ester, carboxylic acid aryl ester, sulphonic acid alkyl ester and sulphonic acid aryl ester groups.

By an alkyl radical, there is understood a branched or unbranched, saturated or unsaturated aliphatic radical with 1 to 6 C atoms which can contain non-ionic substituents, for example the methyl, ethyl, n- and iso-propyl, n-, iso- and tert.-butyl and the various isomeric pentyl and hexyl radicals, as well as vinyl, allyl or propenyl radicals.

Possible anionic radicals $An^-$ are the organic and inorganic anions which are customary for cationic dyestuffs.

Inorganic anions are, for example, fluoride, chloride, bromide and iodide, perchlorate, hydroxyl, radicals of S-containing acids, such as hydrogen sulphate, sulphate, disulphate and aminosulphate; radicals of nitrogen-oxygen acids, such as nitrate; radicals of oxygen-acids of phosphorus, such as dihydrogen-phosphate, hydrogen-phosphate, phosphate and metaphosphate; radicals of carbonic acid such as bicarbonate and carbonate; further anions of oxygen-acids and complex acids, such as methosulphate, ethosulphate, hexafluosilicate, cyanate, thiocyanate, ferrocyanide, ferricyanide, trichlorozincate and tetrachlorozincate, tribromozincate and tetrabromozincate, stannate, borate, divanadate, tetravanadate, molybdate, tungstate, chromate, bichromate and tetrafluoborate, as well as anions of esters of boric acid, such as of the glycerine ester of boric acid, and of esters of phosphoric acid, such as of the methyl-phosphate.

Organic anions are, for example, anions of saturated or unsaturated aliphatic, cycloaliphatic, aromatic and heterocyclic carboxylic acids and sulphonic acids, such as radicals of acetic acid, chloroacetic acid, cyanoacetic acid, hydroxyacetic acid, aminoacetic acid, methylaminoacetic acid, aminoethyl-sulphonic acid, methylaminoethyl-sulphonic acid, propionic acid, n-butyric acid, 1-butyric acid, 2-methylbutyric acid, 2-ethyl-butyric acid, dichloroacetic acid, trichloroacetic acid, trifluoroacetic acid, 2-chloropropionic acid, 3-chloropropionic acid, 2-chlorobutyric acid, 2-hydroxypropionic acid, 3-hydroxypropionic acid, O-ethylglycollic acid, thioglycollic acid, glyceric acid, malic acid, dodecyltetraethyleneglycol-ether-propionic acid, 3-(nonyloxy)propionic acid, 3-(isotridecyloxy)-propionic acid, 3-(isotridecyloxy)-diethyleneglycol-ether-propionic acid, the etherpropionic acid of an alcohol mixture with 6 to 10 carbon atoms, thioacetic acid, 6-benzoylamino-2-chlorocaproic acid, nonylphenoltetraethyleneglycol-ether-propionic acid, nonylphenol-diethyleneglycol-ether-propionic acid, dodecyltetraethyleneglycol-ether-propionic acid, phenoxyacetic acid, nonylphenoxyacetic acid, n-valeric acid, i-valeric acid, 2,2,2-trimethylacetic acid, n-caproic acid, 2-ethyl-n-caproic acid, stearic acid, oleic acid, ricinoleic acid, palmitic acid, n-pelargonic acid, lauric acid, a mixture of aliphatic carboxylic acids with 9 to 11 carbon atoms (Versatic Acid 911 of SHELL), a mixture of aliphatic carboxylic acids with 15 to 19 carbon atoms (Versatic Acid 1519 of SHELL), coconut fatty acid first runnings, undecanecarboxylic acid, n-tridecanecarboxylic acid and a coconut fatty acid mixture; acrylic acid, methacrylic acid, crotonic acid, propargylic acid, oxalic acid, malonic acid, succinic acid, glutaric acid, adipic acid, pimelic acid, suberic acid, azelaic acid, the isomer mixture of 2,2,4- and 2,4,4-trimethyladipic acid, sebacic acid, isosebacic acid (isomer mixture), tartaric acid, citric acid, glyoxylic acid, dimethyl-ether-$\alpha,\alpha'$-dicarboxylic acid, methylene-bis-thioglycollic acid, dimethylsulphide-$\alpha,\alpha$-dicarboxylic acid, 2,2'-dithio-di-n-propionic acid, fumaric acid, maleic acid, itaconic acid, ethylenebis-iminoacetic acid, nitrolosulphonic acid, methanesulphonic acid, ethanesulphonic acid, chloromethanesulphonic acid, 2-chloroethanesulphonic acid and 2-hydroxyethanesulphonic acid and Mersolate, that is to say $C_8$–$C_{15}$ paraffinsulphonic acid obtained by chlorosulphonation of paraffin oil.

Suitable anions of cycloaliphatic carboxylic acids are, for example, the anions of cyclohexanecarboxylic acid and cyclohexene-3-carboxylic acid and anions of araliphatic monocarboxylic acids are, for example, anions of phenylacetic acid, 4-methylphenylacetic acid and mandelic acid.

Suitable anions of aromatic carboxylic acids are, for example, the anions of benzoic acid, 2-methylbenzoic acid, 3-methylbenzoic acid, 4-methylbenzoic acid, 4-tert.-butylbenzoic acid, 2-bromobenzoic acid, 2-chlorobenzoic acid, 3-chlorobenzoic acid, 4-chlorobenzoic acid, 2,4-dichlorobenzoic acid, 2,5-dichlorobenzoic acid, 2-nitrobenzoic acid, 3-nitrobenzoic acid, 4-nitrobenzoic acid, 2-chloro-4-nitrobenzoic acid, 6-chloro-3-nitro-benzoic acid, 2,4-dinitrobenzoic acid, 3,4-dinitrobenzoic acid, 3,5-dinitrobenzoic acid, 2-hydroxybenzoic acid, 3-hydroxybenzoic acid, 4-hydroxybenzoic acid, 2-mercaptobenzoic acid, 4-nitro-3-methylbenzoic acid, 4-aminobenzoic acid, 5-nitro-2-hydroxybenzoic acid, 3-nitro-2-hydroxybenzoic acid, 4-methoxybenzoic acid, 3-nitro-4-methoxybenzoic acid, 4-chloro-3-hydroxybenzoic acid, 3-chloro-4-hydroxybenzoic acid, 5-chloro-2-hydroxy-3-methyl-benzoic acid, 4-ethylmercapto-2-chlorobenzoic acid, 2-hydroxy-3-methylbenzoic acid, 6-hydroxy-3-methyl-benzoic acid, 2-hydroxy-4-methylbenzoic acid, 6-hydroxy-2,4-dimethylbenzoic acid, 6-hydroxy-3-tert.-butylbenzoic acid, phthalic acid, tetrachlorophthalic acid, 4-hydroxyphthalic acid, 4-methoxyphthalic acid, isophthalic acid, 4-chloroisophthalic acid, 5-nitro-isophthalic acid, terephthalic acid, nitroterephthalic acid and diphenyl-3,4-carboxylic acid, o-vanillic acid, 3-sulphobenzoic acid, benzene-1,2,4,5-tetracarboxylic acid, naphthalene-1,4,5,8-tetracarboxylic acid, biphenyl-4-carboxylic acid, abietic acid, phthalic acid mono-n-butyl ester, terephthalic acid monomethyl ester, 3-hydroxy-5,6,7,8-tetrahydronaphthalene-2-carboxylic acid, 2-hydroxy-1-naphthoic acid and anthraquinone-2-carboxylic acid.

Suitable anions of heterocyclic carboxylic acids are, for example, the anions of pyromucic acid, dehydromucic acid and indolyl-(3)-acetic acid.

Suitable anions of aromatic sulphonic acids are, for example, the anions of benzenesulphonic acid, benzene-1,3-disulphonic acid, 4-chlorobenzenesulphonic acid, 3-nitrobenzenesulphonic acid, 6-chloro-3-nitro-benzenesulphonic acid, toluene-4-sulphonic acid, toluene-2-sulphonic acid, toluene-ω-sulphonic acid, 2-chlorotoluene-4-sulphonic acid, 1-hydroxybenzenesulphonic acid, n-dodecylbenzenesulphonic acid, 1,2,3,4-tetrahydronaphthalene-6-sulphonic acid, naphthalene-1-sulphonic acid, naphthalene-1,4-disulphonic acid, or -1,5-disulphonic acid, naphthalene-1,3,5-trisulphonic acid, 1-naphthol-2-sulphonic acid, 5-nitronaphthalene-2-sulphonic acid, 8-aminonaphthalene-1-sulphonic acid, stilbene-2,2'-disulphonic acid and biphenyl-2-sulphonic acid.

A suitable anion of heterocyclic sulphonic acids is, for example, the anion of quinoline-5-sulphonic acid.

Further possibilities are the anions of arylsulphinic, arylphosphonic and arylphosphonous acids, such as benzenesulphinic and benzenephosphonic acid.

Colourless anions are preferred. For dyeing from an aqueous medium, those anions which do not excessively impair the solubility of the dyestuff in water are preferred. For dyeing from organic solvents, those anions which promote the solubility of the dyestuff in organic solvents or at least do not affect it adversely are frequently also preferred.

The anion is generally determined by the manufacturing process and by the purification of the crude dyestuff which may have been carried out. In general, the dyestuffs are present as halides (especially as chlorides or bromides) or as methosulphates, ethosulphates, sulphates, benzenesulphonates or toluenesulphonates or acetates. The anions can be replaced by other anions in a known manner.

Dyestuffs of the general formula (I) can be manufactured by condensation of a compound of the general formula

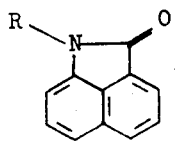

VII wherein
R has the meaning indicated in the formula (I) and
R and/or the naphthalene ring can contain non-ionic substituents,
with an aromatic amine of the general formula

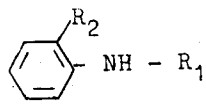

VIII wherein
$R_1$ and $R_2$ have the meaning indicated in the formula (I) and
$R_1$ and $R_2$ and the benzene ring can contain non-ionic substituents,
in a manner which is in itself known, including the use of a condensation agent or condensation agent mixture which yields an anion $An^{(-)}$.

Examples of suitable condensation agents are phosphorus oxychloride, phosphorus trichloride, phosphorus pentachloride, tin tetrachloride, titanium tetrachloride and phosgene, with or without the addition of aluminium chloride, phosphorus pentoxide, zinc chloride and boron fluoride. The condensation can be carried out in the presence or absence of inert diluents, such as chlorobenzene and dichlorobenzene, toluene and xylene, at temperatures between about 50° and 150°C.

A variant of the process consists of using, in place of a naphtholactam-(1,8) of the formula (VII), a functionally equivalent compound of the general formulae

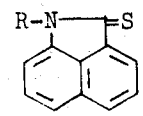

IX

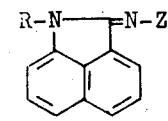

X or

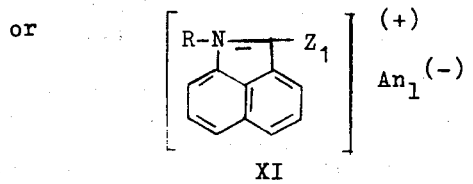

XI

In the formulae (IX), (X) and (XI)
R has the meaning already indicated,
Z is any desired radical,
$Z_1$ is a radical which can be split off as an anion, for example an alkylmercapto group or a chlorine atom and
$An_1^{(-)}$ is an anion.

A further variant consists of employing, instead of the secondary amine (VIII), a compound which under the condensation conditions can change into such an amine or can form a dyestuff which can subsequently be converted into a dyestuff of the formula (I). Such compounds are, for example, acyl derivatives of the amines (VIII), which react with hydrolytic elimination of the acyl radical, or derivatives of the amines (VIII) which contain, on the nitrogen atom, protective groups which can be removed in another manner, which is in itself known, for example the protective groups known from peptide synthesis.

Another process for the manufacture of the new dyestuffs is characterised in that a compound of the general formula

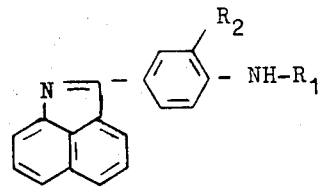

XII wherein
$R_1$ and $R_2$ have the meaning indicated in the formula (I) and the cyclic and acyclic radicals can contain non-ionic substituents and other, optionally non-ionically substituted, carbocyclic or heterocyclic rings can be fused to the rings, or an acyl derivative of the general formula

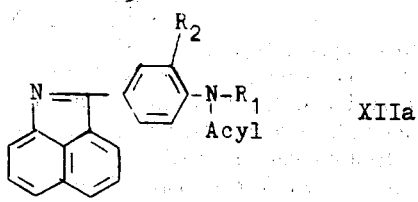

XIIa is treated, in a suitable solvent, such as benzene, toluene, xylene, chlorobenzene or dichlorobenzene, nitrobenzene, dioxane, chloroform, dimethylformamide and N-methylpyrrolidone, with an alkylating agent such as dimethyl sulphate, diethyl sulphate, toluenesulphonic acid methyl ester, ethyl ester, n-propyl ester, β-chloroethyl ester or β-cyanoethyl ester, β-bromopropionitrile, allyl bromide, β-dimethylaminoethyl chloride or β-chloroethyl-methyl-ether, and the acyl radical is subsequently removed by hydrolysis, if appropriate.

A further process for the manufacture of dyestuffs according to the invention is characterised in that compounds of the general formula

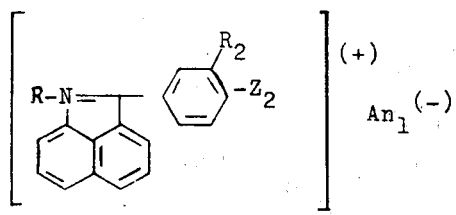

XIII wherein
R and R$_2$ have the meaning already indicated,
Z$_2$ is a radical which can be split off as an anion, preferably a halogen atom, and
An$_1$ is an anion,
are condensed with amines of the general formula

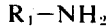    XIV or with amides derived therefrom, of the general formula

    XV wherein
Me is an equivalent of an electropositive metal such as lithium, sodium, potassium, calcium, barium or aluminium.

Compounds of the formula XIII are accessible in accordance with the process of German Offenlegungsschrift (German Published Specification) No. 1,445,730 (Example 6).

Suitable starting materials of the formula (VII) are, for example: N-methyl-, N-ethyl-, N-iso-propyl-, N-n-propyl-, N-iso-butyl-, N-n-butyl-, N-iso-amyl-, N-n-hexyl-, N-cyclohexyl-, N-2-trimethylene-, N-benzyl-, N-β-phenylethyl-, N-γ-phenylpropyl-, N-phenyl-, N-4'-methylphenyl-, N-4'-methylbenzyl-, N-β-cyanoethyl-, N-β-chloroethyl-, N-β-methoxyethyl-, N-β-hydroxycarbonylethyl-, N-ethoxycarbonylmethyl- and N-allyl-naphtholactam-(1,8), their monochloro and monobromo derivatives substituted in the naphthalene ring in the p-position to the nitrogen, 4-methoxy-, 4-ethoxy-, 4-hydroxy-, 4-acetylamino-, 4-dimethylamino-, 4-methylsulphonylamino-, 4-amidosulphonyl-, 4-dimethylamidosulphonyl-, 4-cyano-, 4-methylmercapto-N-ethyl-naphtholactam-(1,8), 4,5-dichloro-N-methyl-naphtholactam-(1,8), 2,4,-dibromo-N-ethyl- and N-n-butyl-naphtholactam-(1,8), 6-methylamino-N-methyl-naphtholactum-(1,8) and 2-ethyl-N-methyl-naphtholactam-(1,8).

Suitable aromatic amines of the formula (VIII) are, for example, N-alkylanilines such as methyl-, ethyl-, n- and iso-propyl-, n-, iso- and tert.-butyl-, n- and iso-amyl-, n-hexyl- and -neo-pentyl-aniline, N-cyclohexylaniline, N-2'-methylcyclohexylaniline, N-benzyl-aniline, N-4'-methyl-, N-4'-methoxy-, N-4'-ethoxy-, N-3',-4'-dichloro-, n-3',4'-di-methoxy-, N-2',4'-dimethoxy-, N-2'-methyl- and N-3'-methylbenzylaniline, N-β-phenylethyl- and N-γ-phenylpropyl-aniline, N-β-cyanoethyl-, N-β-chloroethyl-, N-β-amidocarbonylethyl-, N-β-methoxycarbonyloxyethyl-, N-β-ethoxycarbonylethyl-, and N-β-dimethylaminoethyl-aniline, N-methyl-, N-ethyl-, N-iso-propyl and N-n-butyl-o-toluidine, -o-ethylaniline, -o-anisidine and -o-phenetidine, N-benzyl- and N-2'-methylbenzylaniline, -o-methylaniline, -o-chloroaniline and -o-hydroxyaniline, N-allyl-, N-n-butyl-, N-β-chloroethyl- and N-γ-hydroxypropyl-hydrochinone-dimethyl- and -diethyl-ether, N-ethyl-p-xylidine, 3-chloro-, 3-methoxy-, 3-methyl-, 3-hydroxy- and 3-methoxycarbonylamino-N-iso-butyl-aniline, N-methyl-, N-ethyl-, N-β-cyanoethyl- and N-β-hydroxyethyl-2-methoxy-5-methyl-aniline, 2-ethylamino-diphenylmethane and 2-benzyloxy-N-ethyl-aniline.

The new dyestuffs are suitable for dyeing, printing and bulk dyeing materials which consist wholly or predominantly of polymerised unsaturated nitriles such as acrylonitrile and vinylidene cyanide or of acid-modified polyesters or of acid-modified polyamides. They are furthermore suitable for the customary known applications of cationic dyestuffs, such as dyeing and printing cellulose acetate, coir, jute, sisal and silk, tannin-treated cotton and paper, for the manufacture of ball pen pastes and rubber stamp inks and for use in flexographic printing. The dyeings and prints on the firstmentioned materials, especially on polyacrylonitrile, are distinguished by their very high level of fastness, especially by very good fastness to light, wet processing, rubbing, decatising, sublimation and perspiration. The dyestuffs are furthermore distinguished by their exceptionally uniform fibre affinity which permits the manufacture of completely even dyeings in a simple manner.

Dyestuffs of the general formula (III) in which R$_7$ and R$_8$ represent an alkoxy radical with at most 4 C atoms are furthermore distinguished by a very desirable bathochromic effect. A further advantage of these dyestuffs is their good "evening colour", that is to say the colour shade does not change undesirably in artificial light. Since these dyestuffs furthermore possess particularly good solubility and show a very high fibre affinity and particularly high yield (colour strength), and since they are furthermore particularly stable towards hydrolysing influences, for example against accidental incorrect setting of the pH-value of the dyeing liquor, they are of particular industrial interest because of the combination of these valuable properties.

The parts mentioned in the examples are parts by weight; the temperatures are given in degrees Centigrade.

EXAMPLE 1

276 parts of 4-bromo-N-ethyl-naphtholactam are stirred with 800 parts of phosphorus oxychloride and 150 parts of phosphorus pentoxide. 175 parts of N- ethyl-o-anisidine are run in at 60° to 85°. The reaction is strongly exothermic. The mixture is stirred for 1 hour at about 85° and is allowed to cool, and the excess condensation agent is decomposed by introducing the mixture into 5,000 – 8,000 parts of water and stirring for several hours. Hereupon the crude dyestuff initially separates out as a resin which is purified by recrystallisation from 5,000 parts of water with the addition of active charcoal. The dyestuff is salted out with sodium chloride. It corresponds to the formula

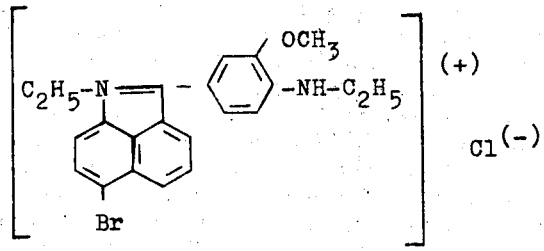

and dyes materials of polyacrylonitrile, acid-modified polyesters and acid-modified polyamides, give a blue having very good fastness properties.

If instead of the abovementioned naphtholactam derivative the particular equivalent amount of N-methyl-, N-iso-propyl, N-n-propyl-, N-n-butyl-, N-n-amyl-, N-cyclohexyl- or N-β-cyanoethyl-4-bromo- (or 4-chloro-)-naphtho-lactam-(1,8) or N-phenyl-, N-benzyl- or N-4′-methoxycarbonylbenzylnaphtholactam-(1,8) is used, and in other respects the procedure is unchanged, valuable blue dyestuffs are again obtained.

EXAMPLE 2:

A mixture of 27.6 parts of 4-bromo-N-ethyl-naphtholactam, 20 parts of monoethylamino-hydroquinone-dimethylether, 80 parts of phosphorus oxychloride and 15 parts of phosphorus pentoxide is stirred for 45 minutes at 80° and thereafter poured into 1,000 parts of ice water. The crude product which separates out is recrystallised from 200 parts of water with the addition of 5 parts of active charcoal. The dyestuff of the formula

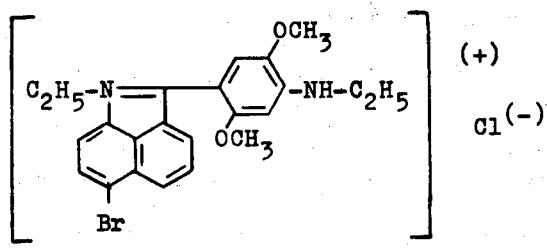

is obtained, which dyes polyacrylonitrile in a greenishtinged blue having very good fastness properties.

If instead of the abovementioned naptholactam derivative the particular equivalent amount of N-methyl-, N-ethyl-, N-iso-propyl-, N-n-propyl-, N-n-butyl-, N-β-phenylethyl-, N-β-chloroethyl-, N,2-trimethylene-, N-ethoxycarbonylmethyl- or N-allylnaphtholactam-(1,8) is used and the procedure is in other respects unchanged, very fast blue to greenish-tinged blue dyestuffs are again obtained.

If, on the other hand, instead of the monoethylaminohydroquinone-dimethyl-ether, N-methyl-, N-ethyl-, N-isobutyl-, N-β-chloroethyl- or N-β-cyanoethyl-1-aminonaphthalene or one of the following amines is used in equivalent amount, fast blue dyestuffs are again obtained:

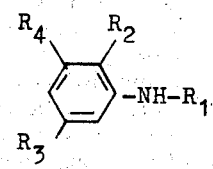

| R$_1$ | R$_2$ | R$_3$ | R$_4$ |
|---|---|---|---|
| Methyl | Ethoxy | Ethoxy | Hydrogen |
| iso-Propyl | Methoxy | Methoxy | " |
| n-Butyl | " | " | " |
| n-Hexyl | " | " | " |
| β-Chloroethyl | " | " | " |
| β-Cyanoethyl | " | " | " |
| β-Methoxy-carbonyl-ethyl | " | 41 | " |
| β-Phenylethyl | " | " | " |
| Benzyl | " | " | " |
| βCyanoethyl | " | Hydrogen | " |
| " | Benzyloxy | " | " |
| " | Hydroxy | " | " |
| Ethyl | n-Butoxy | n-Butoxy | " |
| " | iso-Propyl | Hydrogen | " |
| " | Methyl | Methyl | " |
| " | Ethyl | Hydrogen | " |
| iso-Butyl | Hydrogen | Hydrogen | Methoxy |
| β-Cyanoethyl | " | " | Methoxycarbonyl-amino |
| " | " | " | Dimethylamido-carbonylamino |
| Cyclohexyl | " | " | Ethoxycarbonyl-amino |
| Ethyl | Benzyl | " | Hydrogen |
| " | Methoxy | Chlorine | " |
| " | Methyl | Hydroxy | " |
| " | " | Methoxycar-bonylamino | " |
| " | " | Dimethyl-amidocar-bonylamino | " |

EXAMPLE 3:

A mixture of 100 parts of iso-butylaniline, 500 parts of phosphorus oxychloride, 50 parts of phosphorus pentoxide and 138 parts of N-ethyl-4-bromo-naphtholactam(1,8) is stirred for 15 minutes at 90° to 95°. After cooling to about 75° the mixture is poured into 5,000 parts of the ice water. After stirring for at least 1 hour, 975 parts of concentrated sodium hydroxide solution are added dropwise below 25°. The dyestuff which has separated out is freed of yellow impurities by recrystallisation from water. It corresponds to the formula

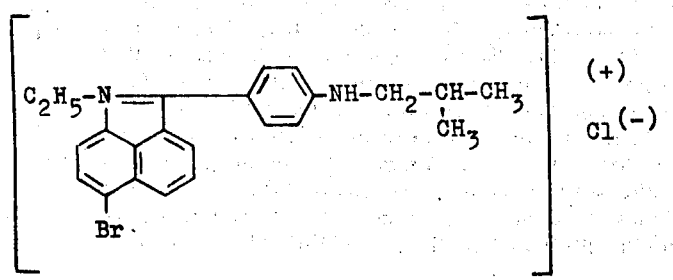

and dyes materials of polyacrylonitrile, acid-modified polyesters and acid-modified polyamides in a fast blue-violet.

If instead of N-ethyl-4-bromo-naphtholactam the particular equivalent amount of n,2-trimethylene-naphtholactam or of its 4-chloro or 4-bromo derivative is used and the procedure is otherwise unchanged, valuable new dyestuffs are again obtained, which yield fast violet or blue-violet dyeings on the materials mentioned.

EXAMPLE 4:

23.2 parts of N-ethyl-4-chloro-naphtholactam-(1,8) and 20.6 parts of N-β-cyanoethyl-amino-hydroquinone-dimethylether are stirred with 90 parts of phosphorus oxychloride. Starting at 20° to 25°, 15 parts of phosphorus pentoxide are added in portions, in the course of which the temperature rises to about 60°. The mixture is carefully heated to 85°, kept for one hour at this temperature, then allowed to cool and poured into about 800 parts of ice water. The crude dyestuff separates out. After complete hydrolysis of the phosphorus oxychloride, the aqueous liquor is decanted and the dyestuff is purified by recrystallisation from water with the addition of charcoal. It corresponds to the formula fluxing with 7.5 parts of phosphorus oxychloride and 22 parts of tin tetrachloride. The temperature is raised to 130° by distilling off a small part of the condensation agent mixture and is kept at about 130° for 10 minutes.

The mixture is then allowed to cool to approx. 60° and 750 parts of chloroform are added. The whole is allowed to boil for 10 to 20 minutes, the chloroform which has cooled is decanted and the residue which has remained insoluble in chloroform is repeatedly extracted by boiling with 400 parts of water at a time. On addition of zinc chloride solution to the combined fitrates, the dyestuff of the formula

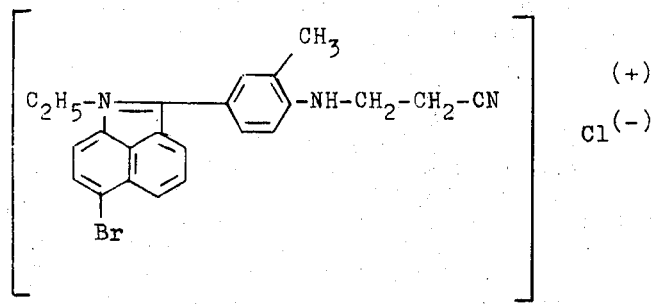

is obtained, which dyes polyacrylonitrile in a fast blueviolet.

If instead of the abovementioned toluidine N-β-cyanoethyl-o-phenetidine is used a dyestuff which dyes polyacrylonitrile and acid-modified polyester in a fast blueviolet is again obtained.

EXAMPLE 6.

An aqueous dyebath containing, per liter, 0.75 g of 30% strength acetic acid, 0.40 g of sodium acetate and 0.25 g of the dyestuff of the formula

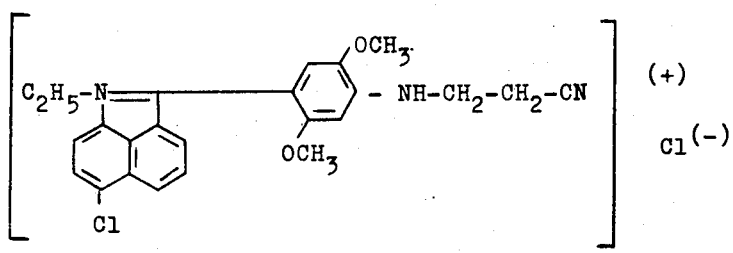

and dyes polyacrylonitrile in a blue having very good fastness properties.

Instead of N-β-cyanoethyl-amino-hydroquinonedimethyl-ether it is also possible to use the particular equivalent amount of the corresponding diethyl-, di-isopropyl- or di-n-butyl-ether; the products are manufactured in the usual manner by addition of acrylonitrile to the primary amines obtainable according to known processes

EXAMPLE 5:

13.8 N-ethyl-4-bromo-naphtholactam-(1,8) and 8 parts of N-β-cyanoethyl-o-toluidine are heated to re-

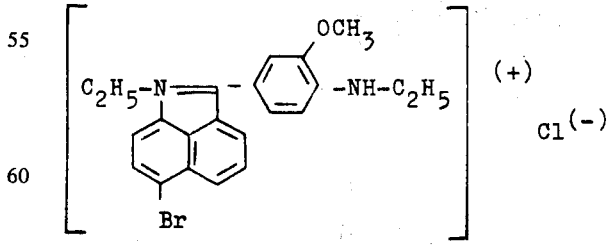

is charged, at approx, 45°, with the amount of polyacrylonitrile fibres corresponding to a liquor ratio of 1:40, heated to the boil over the course of 20 to 30 minutes and kept at this temperature for 30 to 60 minutes. After rinsing and drying the fibres, a blue dyeing having very good fastness properties is obtained.

EXAMPLE 7:

Acid-modified polyglycol terephthalate fibres of the DACRON 64 type (DuPont), or as described in Belgian Patent Specification No. 549,179 and in U.S. Patent Specification No. 2,893,816, are introduced at 20°, in a liquor ratio of 1:40, into an aqueous bath which per liter contains 3 g of sodium sulphate, 0.5 to 2 g of an oleyl-polyglycol-ether (50 mols of ethylene oxide), 2.5 to 5 g of diphenyl and 0.3 g of the dyestuff of the formula of Example 6, and which has been adjusted to a pH-value of 4.5 to 5.5 with acetic acid. The bath is heated to 98° over the course of 30 minutes and kept at this temperature for 60 minutes. Thereafter the fibres are rinsed and dried. A fast blue dyeing is obtained

EXAMPLE 8:

0.75 g of the dyestuff of the formula of Example 6 are worked into a paste with a 20-fold amount of hot water, with addition of a little acetic acid, in a dyeing beaker of 500 ml capacity located in a heated waterbath and the paste is dissolved in hot water. The dyeing liquor is further mixed with 0.5 g of the reaction product of 50 mols of ethylene oxide with 1 mol of oleyl alcohol and is made up to 500 ml with cold water. The pH-value of the dyeing liquor is adjusted to 4.5 – 5 with acetic acid or sodium acetate.

10 g of piece goods of acid-modified polyamide are constantly agitated in this dyeing liquor whilst raising the temperature to 100° over the course of 15 minutes. The material is dyed for 15 – 20 minutes at the boil, rinsed with cold water and subsequently dried, for example by ironing or in a drying cabinet at 60° – 70°. A material dyed blue is obtained.

EXAMPLE 9:

A polyacrylonitrile fabric is printed with a printing paste of the following composition: 30 parts of the dyestuff of the formula of Example 6,
50 parts of thiodiethylene glycol,
30 parts of cyclohexanol,
30 parts of 30% strength acetic acid,
500 parts of crystalline dextrin,
30 parts of aqueous zinc nitrate solution (d = 1.5) and
330 parts of water.

The resulting print is dried, steamed for 30 minutes and subsequently rinsed. A blue print having very good fastness properties is obtained.

I claim:
1. Cationic dyestuff having the formula

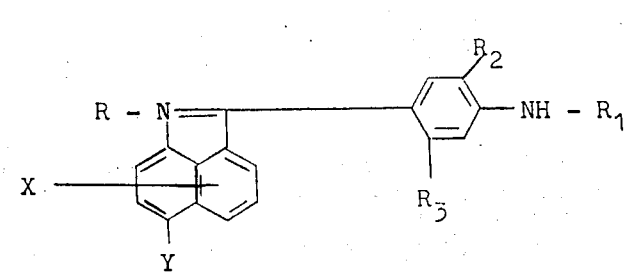

wherein
R is $C_1$-$C_6$-alkyl; cyclohexyl; benzyl; phenylethyl; phenylpropyl; phenyl; methylphenyl; methylbenzyl; allyl; ethyl substituted by nitrile, chloro, $C_1$-$C_4$-alkoxy, carboxy or $C_1$-$C_4$-alkoxycarbonyl; $C_1$-$C_4$-alkoxycarbonylmethyl; or trimethylene bonded to the naphthalene ring in the β-position;

$R_1$ is $C_1$-$C_6$-alkyl; cyclohexyl; benzyl; methylbenzyl; phenylethyl; allyl; or ethyl substituted by nitrile, hydroxy, $C_1$-$C_4$-alkoxy chloro or $C_1$-$C_4$-alkoxycarbonyl;

$R_2$ is hydroxyl; $C_1$-$C_3$-alkyl; $C_1$-$C_4$-alkoxy; benzyl; or benzyloxy;

$R_3$ is hydrogen; chloro; hydroxyl; methyl; $C_1$-$C_4$-alkoxy; methoxycarbonylamino; or dimethylaminocarbonylamino;

X is hydrogen; chloro; bromo; hydroxyl; ethyl; methoxy; ethoxy; acetylamino; methylamino; dimethylamino; methylsulfonylamino; amidosulfonyl; dimethylaminosulfonyl; nitrile; or methylmercapto;

Y is hydrogen; chloro; or bromo.

2. Cationic dyestuff of claim 1, in which R is $C_1$-$C_6$-alkyl; cyclohexyl; benzyl; phenylethyl; phenylpropyl; phenyl; methylphenyl; methylbenzyl; allyl; ethyl substituted by nitrile, chloro, $C_1$-$C_4$-alkoxy, carboxy or $C_1$-$C_4$-alkoxycarbonyl; or $C_1$-$C_4$-alkoxycarbonylmethyl; and $R_1$ is $C_2$-$C_6$-alkyl; cyclohexyl; ethyl substituted by nitrile, chloro, $C_1$-$C_4$-alkoxy, carboxy or $C_1$-$C_4$-alkoxycarbonyl; or $C_1$-$C_4$-alkoxycarbonylmethyl.

3. Cationic dyestuff of claim 1 having the formula

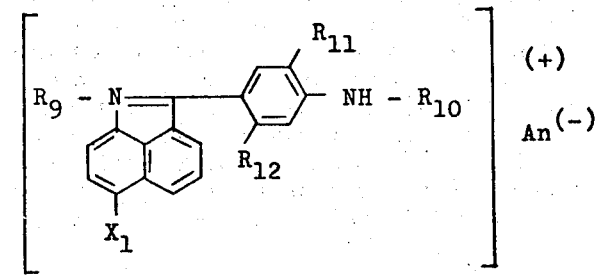

wherein
$R_9$ represents methyl, ethyl, n-propyl, n-butyl, β-cyanoethyl or β-chloroethyl,
$R_{10}$ represents methyl, ethyl, n- and iso-propyl, n- and iso-butyl, n- iso-amyl, β-cyanoethyl, γ-cyanopropyl, β-chloroethyl, β-hydroxycarbonylethyl, β-amidocarbonylethyl, benzyl, 4-methylbenzyl, 4-chlorobenzyl or 4-lower-alkoxybenzyl,
$R_{11}$ represents methyl, ethyl, methoxy or ethoxy,

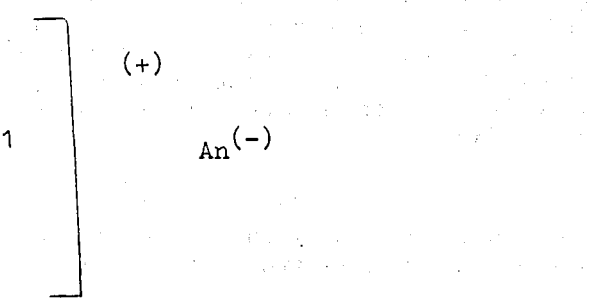

$R_{12}$ represents hydrogen or methyl, ethyl, methoxy or ethoxy, $X_1$ represents hydrogen, chlorine or bromine and $An^{(-)}$ represents an anion.

4. Cationic dyestuff of claim 1 having the formula

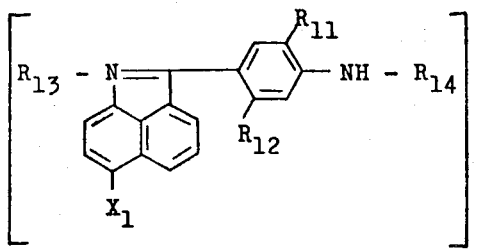

wherein $R_{11}$ represents methyl, ethyl, methoxy or ethoxy, $R_{12}$ represents hydrogen, methyl, ethyl, methoxy or ethoxy, $R_{13}$ represents methyl or ethyl, $R_{14}$ represents ethyl, β-cyanoethyl or β-chloroethyl, $X_1$ represents hydrogen, chlorine or bromine and $An^{(-)}$ represents an anion.

5. Cationic dyestuff of claim 1 having the formula

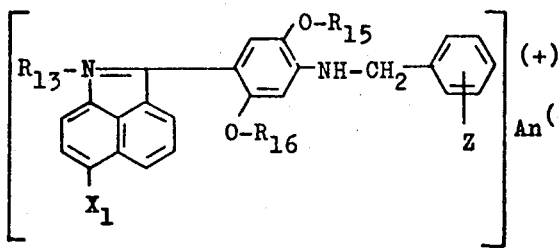

wherein $R_{13}$ represents methyl or ethyl, $R_{15}$ represents methyl or ethyl, $R_{16}$ represents methyl or ethyl, $X_1$ represents hydrogen, chlorine or bromine, Z represents hydrogen, chlorine, methyl, methoxy or ethoxy and $An^{(-)}$ represents an anion.

6. A cationic dyestuff of the formula

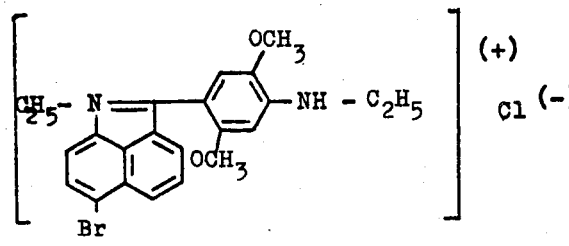

7. A cationic dyestuff of the formula

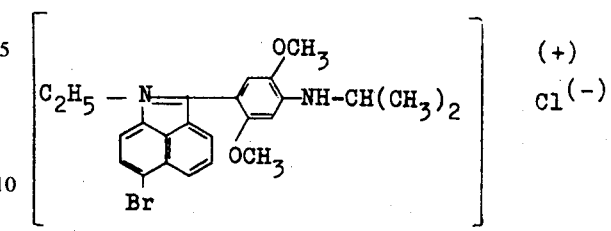

8. A cationic dyestuff of the formula

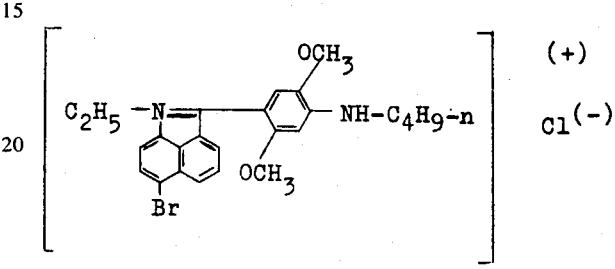

9. A cationic dyestuff of the formula

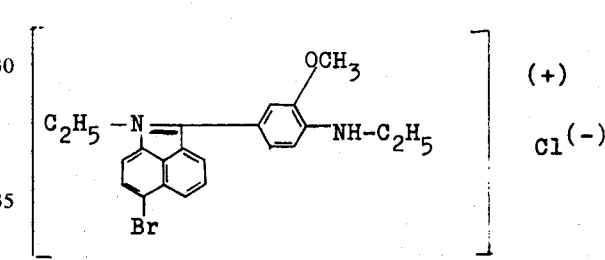

10. A cationic dyestuff of the formula

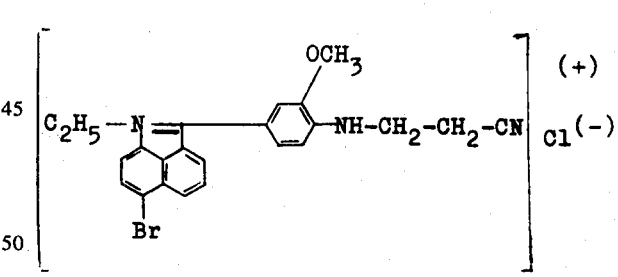

* * * * *